United States Patent [19]

Johnson

[11] Patent Number: 4,489,212

[45] Date of Patent: Dec. 18, 1984

[54] PROCESS FOR PREPARING ALLYL- AND 2-CHLOROPROPYL- OR PROPENYLARENE COMPOUNDS

[75] Inventor: Thomas H. Johnson, Houston, Tex.

[73] Assignee: Shell Oil Company, Houston, Tex.

[21] Appl. No.: 545,303

[22] Filed: Oct. 25, 1983

[51] Int. Cl.$^3$ .................... C07C 41/18; C07C 1/26
[52] U.S. Cl. .................... 568/628; 568/649; 568/654; 568/774; 568/794; 570/127; 570/144; 570/182; 570/193; 585/438; 502/224; 502/231
[58] Field of Search ............ 585/438; 568/654, 628, 568/774, 794, 649; 570/127, 182, 144, 193

[56] References Cited

U.S. PATENT DOCUMENTS 2,910,515 10/1959 Luvisi et al. .................... 568/628 X
3,833,677 9/1974 Grard .............................. 568/628 X Primary Examiner—Bernard Helfin

[57] ABSTRACT

Arenes are reacted with allyl chloride to produce allylarenes and 2-chloropropyl- or propenylarenes using a catalyst comprising a metal oxide substrate having tantalum (V) halide/oxide bound to the surface of the substrate.

9 Claims, No Drawings 4,489,212

PROCESS FOR PREPARING ALLYL- AND 2-CHLOROPROPYL- OR PROPENYLARENE COMPOUNDS

FIELD OF THE INVENTION

This invention relates to a process for preparing allyl- and 2-chloropropyl- or propenylarene compounds from arenes, particularly benzene and substituted benzenes, by reacting the arene compounds with allyl chloride in the presence of a catalyst comprising a metal oxide substrate having tantalum (V) halide/oxide bound to the surface thereof.

BACKGROUND OF THE INVENTION

Aromatic compounds having a three carbon side chain such as an allyl-(—$CH_2CH=CH_2$) or an propenyl-(—$CH=CHCH_3$) side chain find frequent use as flavoring agents, perfumery agents, insecticidal agents and pharmaceutical agents or as intermediates to prepare these agents. Examples of such compounds include p-propenylanisole, p-allylanisole, eugenol, methyl eugenol, isoeugenol, methyl isoeugenol, allyl benzene, propenylbenzene and the like.

Allyl chloride has been used to react with benzene compounds to produce allyl benzene or 2-chloropropylbenzene compounds using Friedel-Crafts type of catalysts. *Friedel-Crafts & Related Reactions,* Vol. 1, G. A. Olah, Ed., pp 892–893, 1963, Interscience, New York. The use of strong Lewis-acids such as $AlCl_3$, $BF_3$, HF and $TaCl_5$ present certain problems in their utilization for commercial applications. These materials are extremely corrosive. They are found either dissolved in or in finely particulate form in the reaction products and require expensive separation processes to maintain product purity. Many of these materials also have a tendency to produce a multitude of products. A process for reacting allyl chloride with arene compounds that would utilize a Friedel-Crafts type of Catalyst which would be "tied down to " an inert support would be very useful from both an environmental point of view, a product quality point of view, a handling point of view, and in alleviating corrosion of plant equipment.

SUMMARY OF THE INVENTION

This invention relates to a process for producing allyl- and 2-chloropropyl- or propenylarene compounds by reacting arenes with allyl chloride in the presence of a catalyst comprising a metal oxide substrate having tantalum (V) halide/oxide bound to the surface of said substrate.

The use of the tantalum (V) halide/oxide-metal oxide composition has several advantages over the "free" tantalum pentahalide, or other Friedel-Crafts type of catalysts such as aluminum chloride or hydrogen fluoride. The use of the tantalum (V) halide/oxide-metal oxide compositions in the instant process minimizes corrosion of process equipment as well as contamination of product alkylate since the tantalum halide is bound to the metal oxide substrate and does not freely move through the system. Resistance to leaching of these compositions is very good. These compositions further minimize the number by-products.

DESCRIPTION OF THE PREFERRED EMBODIMENTS

Illustrative examples of the reactant arenes to be utilized in the instant process are the substituted and unsubstituted benzenes napthalenes, anthracenes and similar compounds. The substituents on these compounds can be any substituents that are not reactive under reaction conditions. Typical substituents include alkyl, hydroxy, alkoxy, cyano, halo, nitro and the like. Preferred carbon numbers of the reactant arene will range from 6 to about 30. Illustrative, but non-limiting examples of preferred arene feedstocks include benzene, toluene, xylene, ethylbenzene, cumene, chlorobenzene, difluoromethybenzene, phenol, anisole, guaiacol, methyl guaiacol, cresols (o, m, p, ), methyl cresols (o, m, p,), etc.

In general the instant process is carried out by contacting the reactant arene with allyl chloride in the presence of a catalyst comprising a metal oxide substrate having tantalum (V) halide/oxide bound to the surface thereof.

The catalysts utilized in the process of the instant invention comprise pentavalent tantalum (also written as tantalum (V), halogen (or halide), oxygen (or oxide) and a solid metal oxide substrate wherein at least one valence of tantalum is bound to oxygen, which oxygen is bound to the substrate, at least one valence of the tantalum is bound to halogen and the remaining tantalum valences are bound to halogen and/or oxygen, which oxygen may or may not be bound to the substrate. The halogens are fluorine, chlorine, bromine, iodine and mixtures thereof. Preferred halogens are fluorine and chlorine.

The metal oxide-tantalum (V) halide/oxide compositions used in the process of the instant invention are preferably prepared by a process comprising reacting under anhydrous conditions a suitable metal oxide substrate which has water chemically bound as hydroxyl and which is substantially free from absorbed water with tantalum pentahalide vapor and thereafter recovering the product. Thus, are produced metal oxide compositions having tantalum (V) halide/oxide bound to the surface thereof. By the term "bound" it is meant herein that the pentavalent tantalum has at least one valence bound to an oxygen which is part of the metal oxide substrate. By the term "surface" it is meant both the external and internal pore surfaces which are accessible to the tantalum pentahalide vapor during the preparation process.

The catalytic compositions utilized in the instant process basically comprise metal oxide substrates having tantalum (V) halides/oxides reactively bound to the surface of said substrate. The halides are selected from the group consisting of fluoride, chloride, bromide, iodide and mixtures thereof. Preferred halides are fluoride and chloride. The compositions are generally prepared by a process which comprises contacting the metal oxide in a substantially anhydrous state with tantalum pentahalide in the vapor state and allowing the vapor to react with the substrate in an atmosphere which is substantially oxygen- and water-free. In the preferred process, sublimation of the tantalum pentahalide is used to put the tantalum pentahalide in the vapor state. Tantalum pentachloride is the preferred sublimation agent, producing the highest metal loadings on the metal oxide substrate. The use of tantalum pentabromides, iodides or fluorides as sublimation agents produces compositions having metal loadings of less than one percent.

A variation of the above process is utilized to produce a composition containing mixed halides, particularly mixed chlorides and fluorides. In this variation, a tantalum (V) chloride/oxide-metal oxide composition is first prepared by reactive sublimation. The tantalum (V) chloride/oxide-metal oxide composition is then contacted wth an oxygen-containing gas or a chemical compound containing oxygen which is weakly covalently bonded to the compound. It is postulated that oxygen replaces part of the halide of the composition. The material is then reacted with a liquid or gaseous fluorinated hydrocarbon which is believed to react preferentially with the oxygen bound only to the tantalum, producing, it is postulated, a composition containing various mixtures of chlorides, fluorides, oxides, oxychlorides, oxyfluorides, oxychlorofluorides, etc., depending on reaction conditions. Analyses of compositions prepared in this fashion show that they contain varying amounts of chlorine and fluorine along with amounts of oxygen (not bound to the substrate) ranging from insignificant to moderate, depending on the degree of fluorination obtained using the fluorinated hydrocarbon. The amount of oxygen remaining can be varied by choice of fluorinated hydrocarbon and reaction conditions. Reaction temperatures and pressures are not critical. Temperatures of room temperature or greater are generally suitable. Different fluorinated hydrocarbons will have different optimum temperatures, pressures and times of contact, and these can readily be determined by routine experimentation. Particularly suitable fluorinated hydrocarbons are the Freons, such as, for example Freon 12 ($CF_2Cl_2$), Freon 14 ($CF_4$), Freon 23 ($CHF_3$), Freon 112 ($CCl_2F—CCl_2F$), Freon 116 ($CF_3—CF_3$), Freon 142 (chlor-difluor-methyl methane), Freon C138 (octafluorocyclobutane) and similar materials. One particular advantage of this process is that it allows the preparation of compositions containing higher amounts of fluoride then does the process using reactive sublimation of tantalum pentafluoride alone. Compositions containing the fluoride are more resistant to oxygen degradation than the compositions containing chloride alone. Thus, when the mixed chloride/fluoride compositions are used as catalysts, the feeds need not be purged of oxygen and air is no longer a poison. Feeds containing oxygen (e.g., $O_2$, peroxide, etc.) however, will still compete for catalyst sites and, hence the observed rates of reaction can be reduced.

As noted above, a modification of the basic catalyst composition of the instant invention can be obtained by contacting the tantalum (V) halide/oxide-metal oxide compositions with oxygen or a compound containing oxygen which is weakly covalently bonded to said compound. Illustrative of said compounds are the peroxides and peroxy compounds, both organic and inorganic, the hypohalide's etc. It is postulated that contact of the instant compositions with oxygen or the indicated oxygen-containing compounds converts part of the halogen on the composition to oxygen which is not bound to the substrate. Thus, there are two possible types of oxygen bound to the pentavalent tantalum of the composition. One type is the oxygen(s) which is bound to the tantalum and to the substrate. This presence of this type of oxygen is required to produce the compositions of the instant invention. The other type of oxygen which optionally may be present is oxygen bound only to the tantalum of the composition. Thus, at least one valence of pentavalent tantalum is bound to oxygen which is bound to the substrate, at least one valence of the tantalum is bound to halogen and the remaining tantalum valences are bound to halogen and/or oxygen which is or is not bound to the substrate. This modification containing the optional oxygen may be effected either inadvertantly or purposefully. It may be effected by contact with oxygen or oxygen-containing compounds present as additives or impurities in feed streams when the compositions are used as catalysts. For many reactions the instant compositions provide for very active catalysts. When these very active catalysts are used in packed-bed flow reactors, they can lead to hot spots and reactor runaway. The activity of the catalyst can be moderated by contact with oxygen or oxygen-containing compounds as described above.

Tantalum (V) halides readily sublime and thus lend themselves to a preferred method of preparation which is called "reactive sublimation" wherein tantalum pentahalide(s) is sublimed into an anhydrous, non-oxidizing atmosphere and allowed to contact and thus react with the metal oxide substrate. In the preparation of these compositions by reactive sublimation, it is important that the reaction be carried out under substantially anhydrous conditions and in a neutral or reducing environment to prevent decomposition of the tantalum chloride.

In this preferred method of preparation the tantalum (V) halide is sublimed by suitable application of temperature and/or vacuum into an essentially anhydrous and oxygen-free atmosphere where it is allowed to contact and react with a substantially anhydrous metal oxide substrate. Any temperature and/or vacuum which causes the tantalum pentahalide to sublime is suitable. Temperatures to about 200° C. are suitable. Frequently the metal oxide substrate is heated during reaction, say up to about 200° C. This heating is not critical to the preparation of the catalyst, but it has been found that by so heating, a more even distribution of the tantalum halide on the metal oxide substrate is effected. After reaction, the metal oxide composition is frequently subjected to an additional period of time at sublimation conditions without the presence of a tantalum pentahalide source. This extra step allows for any unreacted tantalum pentahalide to be sublimed off of the metal oxide composition. The metal oxide substrate before use is frequently subjected to a heat treatment to remove absorbed water. Vacuum can also be applied. Generally, if this pretreatment temperature is too low, free water will remain and if the temperature is too high, sintering of the metal oxide substrate will occur, both of which will adversely affect the catalytic properties of the composition. Generally, the most desirable pretreatment temperatures of the metal oxide substrate range from about 200° to 400° C.

It is postulated that when tantalum penthalide reacts with the hydroxyl group of a metal oxide substrate, that the reaction may be illustrated variously as follows (using chloride as an illustrative halide):

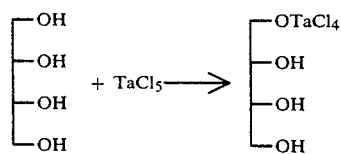

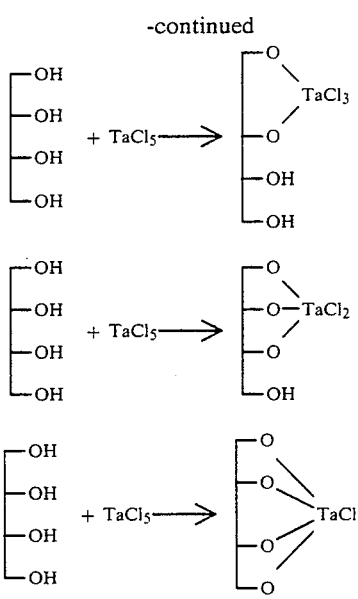

In the final composition a mixture of the above described reaction products will exist. The distribution of the products is believed to be affected by reaction conditions, such as temperature. When tantalum pentahalide is used to prepare the compositions, analysis of chlorine/tantalum ratios in composition containing about 8–17% w tantalum has shown Cl/Ta atomic ratios ranging from about 2.5:1 to about 3.5:1.

Thus, depending on the tantalum halide content desired in the final composition, a tantalum pentachloride vapor is reacted with metal oxide substrate until a part or the whole of the hydroxyl group population of the gel is exhausted.

The reaction between the tantalum pentahalide vapor and the metal oxide substrate is carried out at temperatures ranging at room temperature to elevated temperatures, say 150° to 200° C. or higher. The reaction is normally carried out in an anhydrous, i.e., free from water vapor, atmosphere. The atmosphere should further be a neutral or reducing atmosphere, i.e., oxygen-free. Dispersal of tantalum pentachloride vapor in a vacuum provides a quite suitable atmosphere for reaction with the metal oxide gel.

The metal oxide-tantalum (V) halide/oxide compositions used in the instant invention may be produced in virtually any physical form, as for example, they may be pellets, beads, extrudates, microspheres and in other particular forms, as for example rings, saddles and the like, and in porous or non-porous form.

The metal oxides that are useful as substrates to prepare the catalysts used in the instant process are those inorganic oxides which have hydroxyl groups attached to the surface of the substrate. The hydroxyl groups provide the means by which the tantalum (V) pentahalides are bound to the surface of the substrate. Any metal oxide which has surface hydroxyl (or oxyhydroxyl) groups can be utilized as a substrate.

The term "metal oxide" although used herein in the singular tense, is meant to include the single oxides such as silica, or alumina as well as plural and complex oxides such as silica-alumina, silica-alumina-thoria, zeolites and clays.

The preferred metal oxide substrates are the porous solid inorganic oxides which are conventionally used as catalysts and catalyst supports. Non-limiting examples of these types of materials include those having a major component of silica or alumina or both, such as, for example, alumina and aluminous materials; silica and siliceous materials; clays, particularly open lattice days; and crystalline alumino-silicates (zeolites). Non-limiting examples of aluminous and siliceous materials include, for example, silica-alumina, silica-magnesia, silica-zirconia, silica-titania, alumina-chromia, alumina-ferric oxide, alumina-titania as well as ternary compositions such as, for example, silica-aluminathoria, silica-alumina-zirconia, etc. Non-limiting examples of crystalline aluminosilicates useful as substrates include synthetic zeolites, such as, for example, A, X, Y, L and ASM types such as ZSM-5 and others and naturally occurring zeolites, such as eriorite, faujasite, mordenite, sodalite, cancrinite and others. Non-limiting examples of open lattice clays useful as substrates include bentonite, montmorillonite and others. In a preferred embodiment, the metal oxide should have a major component of silica or aluminum or a mixture of both.

Particularly suitable as substrates are those solid inorganic oxide compositions known as metal oxide gels or gel oxides.

The gel oxides which are particularly suitable for use in preparing the catalytic compositions used in the process of the instant invention are any of the metal oxide gels that are well known in the catalytic art useful as either catalyst base materials or as promoting materials in catalyst compositions. Additionally, the term "metal oxide gel" and "gel oxide" as used herein shall also include the plural oxide gels, i.e., those that contain mixtures of compounds of two or more metal oxides. A metal oxide gel is basically a metal oxide that contains chemically bound water in the form of hydroxyl groups or oxyhydroxyl groups as opposed to absorbed water and water of hydration, although absorbed water and water of hydration may also be present. They are typically prepared by the precipitation of the metal component(s) in an aqueous medium. Upon calcination at sufficiently elevated temperatures, water is given off and the gel is converted to the oxide with two hydroxyl moieties giving one molecule of water and an oxygen is attached to a metal ion. Illustrative of gel oxide base materials used to prepare the composition of this invention are aluminas, silicas, alumina-silicas, alumina-zirconias, silica-zirconias and the like, including naturally occurring hydrous oxide minerals such as clays such as, for example, the kaolinites, the montmorillonites and the like. Among the clays the open lattice clays are particularly desirable. Also included are the zeolites, both natural and synthetic. The structure of the gel oxides can range from amorphous to highly crystalline. Preferred oxide gel materials are selected from the group consisting of alumina, silica, alumina-silica, crystalline aluminosilicates (zeolites) and open lattice clays.

Since the tantalum (V) halide is bound to the surface of the metal oxide by a reaction of the halide with the metal oxide substrate, the metal oxide before reaction must have pendant surface hydroxyl groups attached to the surface. After reaction the metal oxide may or may not have surface hydroxyl groups, depending on the degree of reaction with the tantalum (V) halide.

Prior to use the metal oxide substrate should be substantially free of absorbed water, i.e., "substantially dehydrated or anhydrous". The absorbed or free water is removed by heating the substrate at emperatures ranging from about 100° C. to about 900° C. prior to contact with the tantalum pentachloride vapor. Any environment that provides for drying is suitable such as air, vacuum, inert gas such as nitrogen, etc. The dried substrate should be kept away from a humid atmosphere after drying. It is understood that a dried metal oxide substrate prior to use in preparing the catalysts will still contain chemically bound water in the form of hydroxide and oxyhydroxide.

An aluminum oxide gel is one of the preferred substrates. This alumina can be any of the variety of available aluminas. These are commercially available under various names such as alumina gels, activated aluminas, gamma aluminas, etc. Regarding purity of the alumina, it may be stated that small amounts of impurities are not generally detrimental, and may be beneficial when the impurity is present as a co-gel. In fact "impurities" may be purposely added for catalytic effects. The following table lists several commercial aluminas and their properties which are found suitable.

| Alumina | Surface Area, m$^2$g | Pore Vol., cc/gm | Na, ppm | SO$_4^{50}$, % wt | Fe$_2$O$_3$ % wt | Cl$^-$, % wt |
|---|---|---|---|---|---|---|
| CCI[a] | 252 | 0.8 | 160 | 0.06 | — | 0.02 |
| KA-209[b] | 365 | 0.42 | 600 | 0.03 | — | 0.01 |
| RA-1[c] | 263 | 0.26 | 4700 | 0.02 | 0.18 | — |
| ACCO[d] | 225 | 0.68 | 580 | 0.6 | — | 0.6 |
| Norton | 218 | 0.62 | 51 | 0.03 | — | 0.03 |

[a] Catalysts & Chemicals, Inc., now United Catalysts
[b] Kaiser
[c] Reynolds Corp.
[d] American Cyanamid Corp.
[e] Conoco Corp.
[f] Filtrol Corp.

Silica gel is also another preferred substrate. These are readily available commercially and are essentially substantially dehydrated amorphous silica. These materials are available in various density grades, from low density with surface areas ranging from about 100–300 m$^2$/g to regular density with surface areas up to about 800 m$^2$/g. The commercially available materials are used as dessicants, selective absorbents, catalysts and catalyst supports. Regarding purity of the silica, it may be stated that small amounts of impurities are not generally detrimental and may be beneficial when the impurity is present as a co-gel. In fact, "impurities" may be purposely added for catalytic effects. The following table lists several commercial silicas and their properties which are found suitable.

| Support | Surface Area, m$^2$/g | Pore Vol, cc/g | Density g/cc | Particle Size |
|---|---|---|---|---|
| Davison* Grade 952 SiO$_2$ | 300 | 1.65 | 0.35 | 70 mesh (avg) |
| Davison Grade 59 SiO$_2$ | 300 | 1.15 | 0.38 | 8 mesh |
| Davison Grade 57 SiO$_2$ | 300 | 1.0 | 0.4 | 100 mesh |
| Davison Grade 12 SiO$_2$ | 700 | 0.54 | 0.75 | 20 mesh |
| Davison Grade 03 SiO$_2$ | 750 | 0.43 | 0.7 | 8 mesh (avg) |

*Manufactured by Davison Chemical Div., W. R. Grace & Co.

Other preferred substrates are the aluminosilicates. These materials contain various mixtures of aluminum and silicon oxides. They are readily available commercially and are generally employed as cracking catalysts. Typically they contain from about 50 to about 95, preferably from about 70 to about 90 percent by weight of silica. Illustrations of commercially available alumina-silicas are Davison Grade 980-25 (manufactured by Davison Chemical Division, W. R. Grace & Co.) which contains about 75% SiO$_2$ and 25% Al$_2$O$_3$ and Davison Grade 980-13 which contains about 87% SiO$_2$ and 13% Al$_2$O$_3$. These materials can be prepared in a conventional fashion, as for example by co-precipitation, co-gellation, or by spray drying.

Encompassed within the term "aluminosilicates" are most of the zeolites. The zeolites are found to be specifically useful as substrates. Zeolites are ordered, porous crystalline aluminosilicates having a definite crystalline structure within which there are a large number of small cavities which are interconnected by a number of still smaller channels. Zeolites useful as substrates may be either synthetic or natural. At least 34 species of zeolite minerals are known and the synthetic zeolites number in the hundreds. Any zeolite will be useful as a substrate provided that the zeolite, prior to reaction with tantalum pentahalide, contains chemically bound water in the form of hydroxyl groups. Depending on the state of reaction, the reacted product may contain no hydroxyl groups if all such groups were reacted with the tantalum pentahalide, or there may be unreacted hydroxyl groups still present.

Further descriptions of the preparation of the catalysts used in the instant process are found in application Ser. No. 527,535, filed Aug. 29, 1983, incorporated by reference herein.

The tantalum pentahalides utilized to prepare the compositions used in the process of the instant invention are readily obtainable commercially.

The compositions utilized as catalysts in the instant invention are used in typical fashion, for example, in packed beds or in fluidized beds. In operation, a process stream containing an arene compound such as benzene or a substituted benzene is combined with a process stream containing allyl chloride and passed over a catalyst bed at a temperature ranging from about 10° C. to about 400° C., preferably from about 25° C. to about 150° C. and a pressure ranging from about 1 to about 100 atm. An arene to allyl chloride ratio (molar) of about 2 to about 1 or greater is typically preferred, although higher or lower ratios may be used.

The instant process produces two main compounds; an allyl arene and a 2-chloropropyl- or, depending on reaction conditions, a propenylarene. In certain cases, the presence of heteroatoms, for example, oxygen and nitrogen, in the reactants and/or products facilitates dehydrochlorination of the 2-chloropropyl moiety to the propenyl moiety under the reaction conditions. An example of this dehydrochlorination occurs in the reaction of anisole with allyl chloride. In this case, the 2-chloropropyl moiety will convert to the propenyl moiety under reaction conditions. Apparently, the basicity of the methoxy substituent in the presence of the catalyst is sufficient to allow this spontaneous dehydrochlorination. In other cases, such as for example, the reaction of benzene with allyl chloride, the 2-chloropropyl benzene is produced. This material can readily be dehydrochlorinated to the propenylbenzene in a separate step or during the initial reaction by, for example, the addition of base such as carbonate.

Upon completion of the reaction, the product obtained can be separated into its individual components of product, by-product and reactant by simple means, such as for example, by distillation. The products and by-products, can, if desired, be converted into other useful compounds.

The catalysts described herein, when utilized in the process of the instant invention provide distinct advantages over the use of unsupported materials such as tantalum pentachloride. The catalysts are heterogeneous and can readily be separated from reaction products. The described catalysts are very resistant to leaching, thus, minimizing product contamination and further minimizing corrosion of plant equipment.

The instant process thus comprises an improved process for producing allyl arene and 2-chloropropyl or propenyl arene compounds by reacting arenes and allyl chloride in the presence of a catalyst composition comprising a metal oxide substrate having tantalum (V) halide/oxide bound to the surface of the substrate. The process of the instant invention and the preparation of the compositions used as catalysts in the instant invention will be further described below by the following illustrative embodiments which are provided for illustration and are not to be construed as limiting the invention.

ILLUSTRATIVE EMBODIMENTS

Catalyst Preparation

A. The following illustrates the preparation of a catalyst composition which is utilized in the instant invention. A 200-ml Schlenk flask containing 50–75 g of silica gel (Davison 57, 60–100 mesh) was heated to 300° C. under a vacuum of ca. 0.1 torr for 16–20 h. The flask was moved into a dry box whereupon 6.5 g of the silica was placed on one side of a fritted Schlenk tube. Tantalum chloride (6.0 ) was placed on the other side of the frit. The $TaCl_5$ end of the tube was wrapped with heating tape and then an insulation wrap was installed along with a Thermocouple wire. A vacuum of ca. 0.1 torr was applied at the end of the silica-containing section. The deposition was carried out overnight (16–20 h) at 150° C. with the tube mounted horizontally. The siliceous material was removed in a dry box and then subjected to a vertical sublimation in order to remove any condensed but unreacted $TaCl_5$.

B. The following technique is been found to result in a somewhat more homogeneous catalyst than the above described technique and is utilized where uniformity is important. In this preparative technique a glass scrubbing bottle was modified by internally adding a coarse fritted disc which divided the bottom into an upper section and a lower section. The lower section was fitted with a stoppered connection which allowed it to be charged with tantalum pentachloride and the upper section was fitted with a vacuum stopcock connection which allowed it to be closed off or to be connected to a vacuum. To the modified gas-scrubbing bottle were added about 20 g of $TaCl_5$ to the bottom section and about 60 g of Davison 57 silica ($-20+30$ mesh, pretreated at 300° C. under 0.1 torr vacuum for 12–24 h) to the top section. Both sections were loaded in a dry box containing a nitrogen atmosphere. The bottom section was stoppered and the top section had the vacuum stopcock closed before removing from the dry box. The bottom section of the bottle was immersed into an oil bath and heated at about 150° C. The top section was wrapped with heating tape and heated to about 150° C. A vacuum (ca 0.1 torr) was applied at the top of the bottle. The heating and vacuum phase of the preparation was simultaneous and carried out over a period of 18 h. At the end of 18 h, the bottle (vacuum stopcock closed) was put back into the dry box and 20 g a fresh $TaCl_5$ was added to the bottom section. The rest of the procedure was then repeated for another 18 h. Then the silica was removed, in a nitrogen-filled dry box, and vertically sublimed at 150° C. and 0.1 torr for 18 h. This step was employed to remove any deposited but unreacted $TaCl_5$ on the silica surface. A small ($<200$ mg) of $TaCl_5$ was generally collected on the cold finger of the sublimator.

C. In a variation of the process just described above 24 milliliters of the tantalum (V) chloride-silica composition was added directly to a flow reactor and then subjected to an air flow at 200° C., 100 psi at a GSHV of 10,000 $h^{-1}$ for 30 minutes. Then, $CF_4$ (Freon 14) was passed through the bed at 200° C., 100 psi and a GHSV of 240 $h^{-1}$ for a period of 2 hours. Analysis of the resultant composition of the instant invention by neutron activation showed it to contain about 15.7% w Ta, 3.6% Cl and 0.4% w F.

D. In another variation of the just described process, 12 milliliters of the tantalum (V) chloride-silica composition was added to a fixed-bed flow reactor and treated with air at a flow rate of 4 l/min for 15 minutes at 100 psi and 200° C. The air-treated material was then treated with Freon 12 ($CF_2Cl_2$) at 200° C. and 70 psi at a flow rate of 2.4 l/hr for 5 hours. The flow tube was then sealed and left under an atmosphere of Freon 12 at 200° C., 75 psi for 60 hours. Analysis of the resultant composition of the instant invention by neutron activation showed it to contain about 15.7% w Ta, 1.9% w Cl and 5.7% w F.

Process

A. Benzene Reactant.

To a 50 ml Erlenmeyer flask were added 15 ml of benzene, 1 ml of allyl chloride and 0.5 g of tantalum (V) chloride/oxide-silica catalyst (prepared similar to procedure B above, Davison 57 silica, 300 mg$^2$/g surface area, 1.0 cc 1 g pore volume, 5.0 w % tantalum, $-60$ to $+100$ mesh). The reaction was stirred for one hour at room temperature. Then, the reaction was analyzed by GC ($10' \times \frac{1}{4}''$ SP 2100 column operated at 130° C.) and mass spectroscopy. These analyses showed two products in a 1:1 ratio; allyl benzene and 2-chloropropylbenzene. Conversion of allyl chloride after 1 hour was about 30%.

B. Methyl Guaiacol Reactant.

To a 50 ml Erlenmeyer flask were added 5 ml of 1,2-dimethoxybenzene, 1 ml of allyl chloride and 0.5 g of tantalum (V) chloride/oxide-silica catalyst prepared similar to procedure B above (9.6 wt. % tantalum, $-60$ to 30 100 mesh). The sample was analyzed as above and compared to a known standard of methyl eugenol. The results showed the two products as being methyl eugenol and the 2-chloropropyl analogue.

C. Anisole Reactant.

To a 50 ml Erlenmeyer flask were added 5 ml of anisole, 1 ml of allyl chloride and 0.5 g of tantalum (V) chloride/oxide-silica catalyst prepared similar to procedure B above (9.6% wt. tantalum, $-60$ to $+100$ mesh). The sample was analyzed as above and four products were determined to be present: p-propenylanisol, o-propenl yanisole, p-allylanisole and o-allyanisole.

I claim:

1. A process for reacting an arene with allyl chloride to produce allylarene and 2-chloro- or propenylarene which process comprises contacting said arene with allyl chloride at a temperature ranging from about 10° C. to about 400° C. in the presence of a catalyst which comprises pentavalent tantalum, halogen, oxygen and a metal oxide substrate wherein at least one valence of tantalum is bound to oxygen which is bound to the substrate, at least one valence of tantalum is bound to halogen and the remaining tantalum valences are bound to halogen and/or oxygen which may or may not be bound to the substrate.

2. The process of claim 1 wherein said substrate is silica, alumina, silica-alumina, zeolite, open lattice clay or mixtures thereof and the halogen is chloride or fluoride or mixtures thereof.

3. The process of claim 1 wherein said substrate has a major component of silica or alumina or a mixture thereof and the halogen is chloride or fluoride or a mixture thereof.

4. The process of claim 1 wherein the pressure ranges from 1 to about 100 atm.

5. The process of claim 1 wherein said arene has a carbon number ranging from 6 to about 30.

6. The process of claim 5 wherein said arene is a substituted or unsubstituted benzene.

7. The process of claim 6 wherein said arene is anisole.

8. The process of claim 1 wherein the catalyst is prepared by a process which comprises subliming tantalum pentachloride and reacting in a substantially anhydrous and oxygen-free atmosphere the vapor therefrom with a substantially anhydrous, hydroxyl-containing metal oxide substrate.

9. The process of claim 1 wherein the catalyst is prepared by a process which comprises:
(a) subliming tantalum pentachloride and reacting in a substantially anhydrous and oxygen-free atmosphere the vapor therefrom with a substantially anhydrous, hydroxyl-containing metal oxide substrate,
(b) contacting the product of step (a) with an oxygen-containing gas and,
(c) contacting the product of step (b) with a liquid or gaseous fluorinated hydrocarbon.

* * * * *